United States Patent [19]

Hayakawa et al.

[11] Patent Number: 4,722,778
[45] Date of Patent: Feb. 2, 1988

[54] GAS SENSOR WITH GAS DIFFUSION CHAMBER BETWEEN TWO PLATY SOLID ELECTROLYTE CELLS

[75] Inventors: Nobuhiro Hayakawa; Tetsusyo Yamada; Kazunori Yokota, all of Aichi, Japan

[73] Assignee: NGK Spark Plug Co., Ltd., Nagoya, Japan

[21] Appl. No.: 12,161

[22] Filed: Feb. 9, 1987

[30] Foreign Application Priority Data

Feb. 17, 1986 [JP] Japan ................................. 61-32497

[51] Int. Cl.$^4$ ............................................ G01N 27/58
[52] U.S. Cl. .................................................. 204/410
[58] Field of Search ............... 204/410, 412, 425, 426, 204/1 S

[56] References Cited

U.S. PATENT DOCUMENTS 4,505,806 3/1985 Yamada .............................. 204/425

Primary Examiner—G. L. Kaplan
Attorney, Agent, or Firm—Schwartz, Jeffery, Schwaab, Mack, Blumenthal & Evans

[57] ABSTRACT

The invention relates to a gas sensor having first and second solid electrolyte cells each of which has a solid electrolyte plate, e.g. a zirconia plate, and a pair of porous electrode layers formed on the opposite surfaces of the plate, spacing means to hold the first and second cells in a narrowly spaced, opposite and parallel arrangement and to define a gas chamber, which admits a gas atmosphere subject to measurement, within the gap between the two cells such that the inner electrode layers of the two cells face each other across the gas chamber and means to appropriately restrict diffusion of the gas atmosphere into the gas chamber. Usually one of the two solid electrolyte cells is used as a concentration cell and the other as an ion pump. To prevent unintentional changes in the distance between the two electrode layers facing each other across the gas chamber during the manufacturing process including sintering treatment, at least one support pillar is disposed in the gas chamber so as to fixedly extend from the inner electrode layer of the first cell to the inner electrode layer of the second cell.

11 Claims, 3 Drawing Figures

GAS SENSOR WITH GAS DIFFUSION CHAMBER BETWEEN TWO PLATY SOLID ELECTROLYTE CELLS

BACKGROUND OF THE INVENTION

This invention relates to a gas sensor of the type having a gas diffusion chamber defined in a narrow gap between two platy solid electrolyte cells and provided with gas diffusion restricting means.

Many types of gas sensors using solid electrolytes have been developed and put into practical use for various industrial purposes and also for antipollution purposes.

A relatively recently developed gas sensor is characterized in that a plate-like solid electrolyte cell using a selected solid electrolyte which is conductive to ions of a specific gas and having a pair of electrode layers on the opposite surfaces and another solid electrolyte cell of substantially the same construction are held opposite and parallel to each other so as to define a gas chamber, which admits a gas atmosphere subject to measurement, between the two cells and that the gas chamber is provided with appropriate gas diffusion restricting means. One solid electrolyte cell is used as a concentration cell element and the other cell as an ion pump element. Usually the current for operation of the ion pump cell element is controlled so as to keep the output voltage of the concentration cell element at a predetermined constant level, and the actual value of the pump current is detected as an output signal indicative of the concentration of the specific gas in the gas atmosphere in which the gas sensor is used. For example, U.S. Pat. No. 4,505,806 issued to Yamada discloses an oxygen sensor of this type.

In such a gas sensor the correlation between the output of the sensor and the concentration of the gas to be sensed depends on the effects of the gas diffusion restricting means provided to the gas chamber and also on a gas diffusion restricting effect of the gas chamber itself, which is attributed to thinness of the gas chamber or narrowness of the gap between the two solid electrolyte cells. The effects of the gas diffusion restricting means are determined at the manufacturing stage and can be adjusted even after completion of the manufacturing process. However, the thickness of the chamber cannot be adjusted after the manufacturing process. Furthermore, in industrial manufacture of a large number of gas sensors it is not easy to make the thickness of the gas chamber constant and uniform because of several reasons including some shrinkage or distortion of the solid electrolyte plates at the firing step in the manufacturing process.

SUMMARY OF THE INVENTION

It is an object of the present invention to provide an improved gas sensor which is of the above described type and in which the thickness of the gas chamber is kept accurately and uniformly at the predetermined value even in the case of mass-production.

The present invention provides a gas sensor having first and second solid electrolyte cells each of which has a solid electrolyte plate and a pair of porous electrode layers formed on the opposite surfaces of the solid electrolyte plate, spacing means for holding the first and second solid electrolyte cells in a spaced, opposite and parallel arrangement and defining a gas chamber for admitting a gas atmosphere subject to measurement within the gap between the first and second cells such that the inner one of the electrode layers of the first cell directly faces the inner one of the electrode layers of the second cell across the gas chamber, and gas diffusion restricting means for appropriately restricting diffusion of the gas atmosphere subject to measurement into the gas chamber. According to the invention, the gas sensor further comprises at least one support pillar which is disposed in the gas chamber and is in close contact at its one end with the inner electrode layer of the first solid electrolyte cell and at the opposite end with the inner electrode layer of the second solid electrolyte cell.

Usually the material of the support pillar(s) according to the invention is a ceramic material, and the support pillar(s) may or may not be porous. The gas chamber is provided with either a single support pillar or a plurality of support pillars which are, preferably, substantially uniformly distributed over the entire area of the gas chamber or the electrode layers exposed to the gas chamber. It is suitable to determine the thickness of the gas chamber and the height of the support pillar(s) within the range from 0.01 to 0.2 mm. As to the cross-sectional area of each support pillar and the number of the support pillars, it is suitable that the total contact area between the support pillar(s) and the inner electrode layer of each solid electrolyte cell falls in the range from 0.8 to 20% of the initially exposed area of the electrode layer.

The provision of the support pillar(s) according to the invention is a very sure measure to prevent the distance between the inner electrode layers of the first and second solid electrolyte cells from varying during manufacture of the gas sensor. Therefore, the products of industrial production of a gas sensor according to the invention become very uniform in the output characteristic.

For a gas sensor according to the invention a suitable solid electrolyte is selected according to the kind of gas to be sensed. For example, $\beta$-$Al_2O_3$ is used to produce a sodium gas sensor, and stabilized $ZrO_2$ or a solid solution of $CeO_2$, $ThO_2$ and/or $HfO_2$ is used to produce an oxygen sensor. When an oxygen ion conductive solid electrolyte is used the gas sensor can be used, besides the primary use as an oxygen sensor, for measuring the concentrations of some combustible gases such as $H_2$, CO, $CH_4$, etc.

In gas sensors accoding to the invention, the gas diffusion restricting means provided to the gas chamber may be, for example, a narrow inlet to the gap between the two solid electrolyte cells or at least one aperture which is formed in the spacing means so as to provide communication between the gas chamber and an external gas atmosphere subject to measurement. In the latter case, each aperture may be plugged with a porous material to thereby increase the resistance to gas diffusion.

DESCRIPTION OF THE PREFERRED EMBODIMENTS

Figure 1:
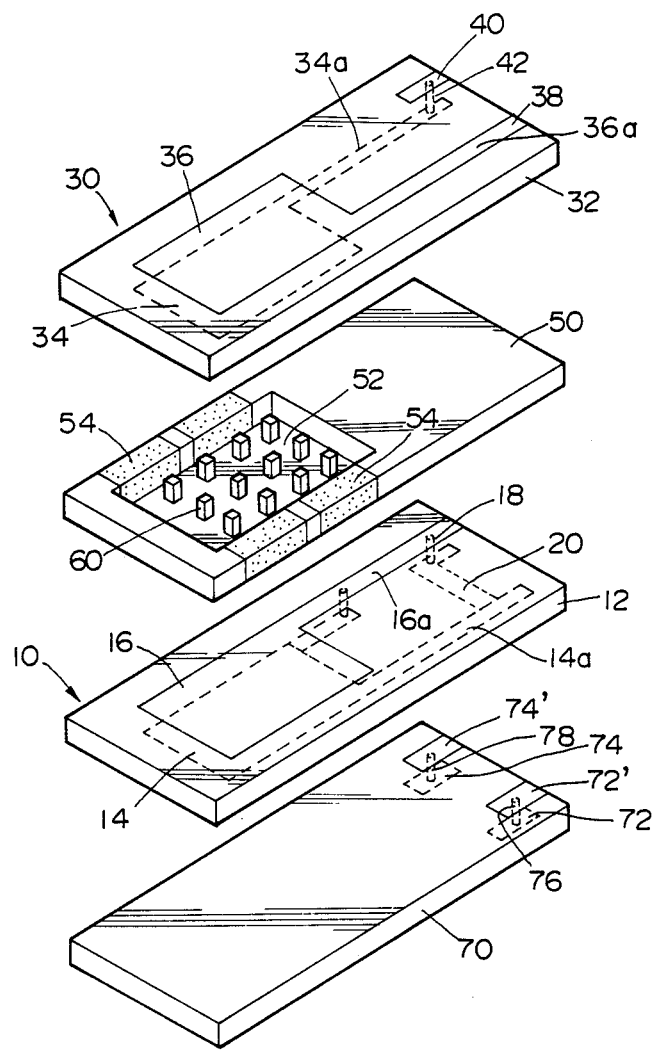
FIG. 1 is an exploded perspective view of a gas sensor as an embodiment of the present invention.

FIG. 1 shows the construction of a gas sensor in which the present invention is embodied. In short, this gas sensor is a laminate of four plate-like parts, namely, a first element 10 which functions as a concentration cell, a second element 30 which functions as an ion pump, a spacer board 50 and a shield board 70. Besides the spacer board 50, a plurality of support pillars 60 according to the invention are disposed in a space between the first and second elements 10 and 30.

The first element 10 has a solid electrolyte plate 12 and a pair of porous electrode layers 14 and 16 formed in an opposite arrangement on the outer and inner surfaces of the plate 12, respectively. A porous insulator layer 20 is formed on the outer surface of the plate 12 so as to extend from a lead portion 14a of the electrode 14 toward the opposite side edge of the plate 12, and a through-hole 18 is bored in the plate 12 so as to provide a passage from a lead portion 16a of the electrode 16 on the inner surface to an end region of the porous insulator layer 20 on the outer surface. The second element 30 has a solid electrolyte plate 32 and a pair of electrode layers 34 and 36 formed in an opposite arrangement on the inner and outer surfaces of the plate 32, respectively. In the gas sensor the electrode layer 34 comes opposite to the electrode layer 16 on the inner surface of the first element 10. The electrode layer 36 on the outer surface of the plate 32 has an elongate lead portion 36a which provides a terminal 38. A lead portion 34a of the electrode layer 34 on the inner surface is connectable to a terminal 40 formed on the outer surface via a through-hole 42 bored in the plate 32. The shield board 70 comes into close contact with the outer surface of the first element 10. This board 70 is formed with a pair of terminals 72 and 74 on the outer surface and a pair of terminals 72' and 74' on the inner surface such that the electrode layers 14 and 16 of the first element 10 can be connected to the terminals 72' and 74', respectively, and then to the terminals 72 and 74 via two through-holes 76 and 78, respectively.

The spacer board 50 is closely sandwiched between the plate-like first and second elements 10 and 30. The spacer board 50 is cut away so as to provide a large through-hole 52 such that the inner electrode layer 16 of the first element 10 directly faces the inner electrode layer 34 of the second element 30 across this hole 52. In the gas sensor the through-hole 52 in the spacer 50 is used as a gas chamber into which a gas atmosphere subject to measurement diffuses. The spacer board 50 is further cut away in the frame-like side marginal regions defining the hole 52, and the cutout sections are replaced by four porous blocks 54 which serve as gas diffusion restricting means. The elongate lead portion 16a of the porous electrode layer 16 on the inner surface of the first element 10 and the porous insulator layer 20 on the outer surface of the first element 10 provides a resistance to leak of the gas from the chamber 52 via the porous electrode layer 16.

In the gas chamber 52 there are twelve support pillars 60 arranged at suitable and nearly equal intervals. The height of these support pillars is equal to the nominal thickness of the spacer 50, so that every support pillar 60 comes into and remain in close contact with the inner electrode layer 16 of the first element 10 and the inner electrode layer 34 of the second element 30. Therefore, the distance between these two electrode layers 16 and 34 becomes invariable and uniform over the entire area. The number of the support pillars 60 is not limited, as mentioned hereinbefore.

The solid electrolyte as the principal material of the first and second elements 10 and 30 is selected, as mentioned hereinbefore, according to the purpose of the gas sensor. The porous electrode layers 14, 16, 34, 36 are usually formed of a noble metal such as platinum or gold, or a mixture of such a noble metal and the solid electrolyte of the plates 12 and 32. These porous electrode layers can be formed by printing a paste containing the electrode material in powder form onto each surface of the solid electrolyte plate by using a conventional thick-film technique and then sintering the printed paste layer. Alternatively, a thin-film technique such as flame spraying, chemical plating or vapor deposition may be used. Both the spacer board 50 and the shield board 70 are ceramics boards. The material of the support pillars 60 is usually ceramics such as, for example, alumina, zirconia, mullite or spinel. When the gas sensor is to be used in such a manner that the electrode 16 of the first element 10 and the electrode 34 of the second element 30 are at the same potential, the support pillars 60 may be formed of an electroconductive material.

A suitable range of the distance between the electrode layer 16 of the first element 10 and the electrode layer 34 of the second element 30 is from 0.01 to 0.2 mm, and a preferable range is from 0.01 to 0.1 mm. The distance between the two electrodes 16 and 34 is determined by the height or thickness of the gas chamber 52. That is, in the actual gas sensor the spacer 50 is a very thin board and the support pillars 60 are very small in height or thickness. If the thickness of the gas chamber 52 is less than 0.01 mm the responsiveness of the gas sensor becomes rather inferior because the gas chamber 52 itself becomes unduly high in its gas diffusion restricting effect. If the thickness of the gas chamber 52 is more than 0.2 mm the responsiveness of the gas sensor becomes inferior because within the gas chamber 52 there arises a considerable difference in partial pressure of the gas subject to measurement, particularly between a laminar region adjacent to the electrode laye 34.

The support pillars 60, which are very thin pieces as mentioned above, can be formed on either the electrode layer 16 of the first element 10 or the electrode layer 34 of the second element 30 by a thick-film technique which may comprise a screen-printing process.

The support pillars 60 are sized and arranged so as to leave a major portion of the electrode layers 16 and 34 exposed. With respect to the initial electrode area facing the gas chamber 52, it is suitable that the total contact area between the support pillars 60 and each electrode layer 16, 34 falls in the range from 0.8 to 20% of the initial electrode area. So far as the proportion of the total contact area is not more 20%, the support pillars 60 do not constitute a substantial obstruction to diffusion of the ga subject to measurement in the gas chamber 52 so that the expected reactions at the electrode surfaces proceed smoothly, and accordingly the output of the gas sensor has a good correlation with the concentration of a specific component of the gas diffused into the gas chamber 52. If the proportion of the total contact area is less than 0.8% the support pillars 60 may be insufficient in mechanical strength.

For some purposes, the gas sensor of FIG. 1 may be modified to provide a means for externally supplying a reference gas, e.g. oxygen, onto the outer surface of the solid electrolyte plate 12 of the first element 10 or a means for generating a reference gas at the electrode layer 14 on the same surface.

EXAMPLE

An oxygen-sensitive air/fuel ratio sensor of the construction shown in FIG. 1 was produced by using the following materials.

The solid electrolyte material of the plates 12 and 32 of the first and second elements 10 and 30 was $ZrO_2$ stabilized with $Y_2O_3$. The electrode layers 14, 16, 34 and 36 were all porous and were all formed of a mixture of Pt and 10 wt % of $ZrO_2$ stabilized with $Y_2O_3$. The material of both the spacer board 50 and the shield board 70 was zirconia. The support pillars 60 were formed of $Al_2O_3$ and had a porous structure.

The solid electrolyte plates 12 and 32 were each 4 mm in width, 25 mm in length and 0.5 mm in thickness. Each of the electrode layers 14, 16, 34 and 36 was 2.4 mm in width and 7.2 mm in length excluding the lead portion. The spacer board 50 was 4 mm in width, 25 mm in length and 60 μm in thickness. The gas chamber 52 was 2.4 mm in width and 7.7 mm in length. The four porous gas diffusion restricting parts 54 were each 1.7 mm in width. The shield board 70 was 4 mm in width, 25 mm in length and 0.5 mm in thickness.

This air/fuel ratio sensor is of use for detecting the actual air/fuel ratio in an internal combustion engine, which may be an automotive engine, from the concentration of oxygen in the exhaust gas. Fundamentally, this air/fuel ratio sensor operates in the following manner.

A predetermined DC voltage (e.g. 5 V) is applied to the first element (sensor element) 10 across the electrodes 14 and 16 through a suitable resistance (e.g. 250 kω) so as to force a predetermined DC current to flow through the solid electrolyte plate 12 from the outer electrode layer 14 toward the inner electrode layer 16. The DC current of such polarity allows oxygen ions to migrate through the solid electrolyte plate 12 from the gas chamber 52 to the outer electrode layer 14 which is covered with the shield board 70 and serves as an accumulator of a reference oxygen partial pressure. The exhaust gas continues to diffuse into the gas chamber 52 through the porous sections 54 of the spacer 50. There will be a difference between the partial pressure of oxygen at the electrode layer 16 exposed to the gas chamber 52 and the reference oxygen partial pressure at the outer electrode layer 14. Then the sensor element 10 generates an electromotive force the magnitude of which depends on the oxygen partial pressure ratio between the inner and outer electrode layers 16 and 14. This electromotive force can be taken out as an output voltage across the electrodes 14 and 16 or across the terminals 72 and 74. The magnitude of such output voltage of the sensor element 10 differs by $10^2$ mV depending on whether the air/fuel ratio in the engine is higher or lower than the stoichiometric ratio (where excess air factor $\lambda=1$), and the output voltage exhibits a sharp and step-wise change if the air/fuel ratio in the engine changes across the stoichiometric value.

The second element or ion pump element 30 is operated with supply of a DC current (will be referred to as the pump current) which flows through the solid electrolyte plate 32 between the opposite electrode layers 34 and 36. The pump current is controlled so as to keep the output voltage of the sensor element 10 at a predetermined constant value by pumping oxygen through the solid electrolyte plate 32 into or from the gas chamber 52. For example, when the air/fuel sensor is an element of a feedback conrol system to control the actual air/fuel ratio in the engine to the stoichiometric value ($\lambda=1$), the pump current is controlled so as to keep the partial pressure of oxygen in the gas chamber 52 at a level corresponding to the oxygen partial pressure in the exhaust gas produced by combustion of a stoichiometric air-fuel mixture, irrespective of the actual partial pressure of oxygen in the exhaust gas flowing outside the air/fuel ratio sensor. The actual value of the pump current under such control is detected to use as an air/fuel ratio indicative output of the air/fuel ratio sensor. In some cases, the pump current supplied to the element 30 is controlleld to a constant value to thereby pump a predetermined constant amount of oxygen into or from the gas chamber 52, and the output voltage of the first element 10 is detected as an air/fuel ratio indicative output of the air/fuel ratio sensor.

With respect to the above described air/fuel ratio sensor, the dependence of the output characteristic of the sensor on the total contact area between the support pillars 60 and each of the electrode layers 16 and 34 was examined by the following experiments.

Figure 2:
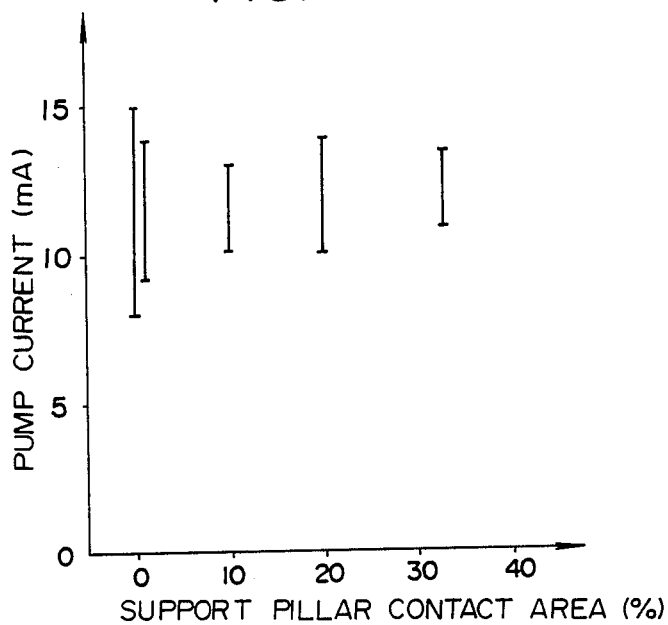
FIG. 2 is a graph showing the relationship between the total cross-sectional area of the support pillars in the gas sensor of FIG. 1 and the amount of dispersion of the output of a number of samples of the gas sensor of FIG. 1 in a stable gas atmosphere.

The total contact area between the support pillars 60 and each of the electrode layers 16, 34 was varied, by varying the number of the support pillars, to 0% (i.e. no support pillar), 0.8%, 10%, 20% and 33% of the initial electrode area. In each case fifty (50) samples of the air/fuel ratio sensor were produced. In the first experiment, every sample sensor was exposed to the atmosphere and the pump current for each sample was controlled so as to adjust the output voltage of the concentration cell element 10 to 450 mV. As the result, the relationship between the proportion of the total contact area and the amount of dispersion of the required pump current with respect to the fifty samples was as shown in FIG. 2. As can be seen in FIG. 2, the amount of dispersion of the output characteristic of the air/fuel ratio sensors decreased by about 50% when the support pillars according to the invention were provided in the gas chamber.

Figure 3:
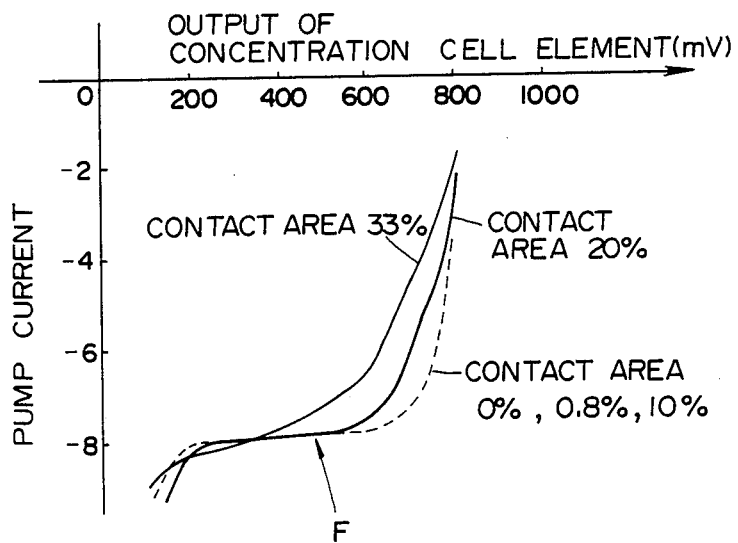
FIG. 3 is a graph showing the dependence of the output characteristic of the gas sensor of FIG. 1 on the total cross-sectional area of the support pillars.

In the second experiment the sample sensors were exposed to the exhaust gas of an automotive engine which was operated with a fuel-rich mixture ($\lambda=0.8$), and the pump current for each sample was controlled so as to allow the concentration cell element 10 to produce a predetermined output voltage which was varied over a range from about 150 mV to about 800 mV. As shown in FIG. 3, the relationship between the output voltage of the concentration cell element and the required pump current was dependent on the proportion of the total contact area between the support pillars and the electrode layer. It is favorable that the output characteristic of the air/fuel ratio sensor becomes flat (with respect to the required pump current), as indicated by the arrow F in FIG. 3, over a wide and intermediate range of the output voltage of the concentration cell element. The experimental result shown in FIG. 3 indicates that the output characteristic becomes better as the proportion of the total contact area is made smaller and particularly when the proportion of the total contact area is not more than 20%.

What is claimed is:

1. In a gas sensor having first and second solid electrolyte cells each of which has a solid electrolyte plate and a pair of porous electrode layers formed on the opposite surfaces of the solid electrolyte plate, spacing means for holding the first and second solid electrolyte cells in a spaced, opposite and parallel arrangement and defining a gas chamber for admitting a gas atmosphere subject to measurement within the gap between the first and second solid electrolyte cells such that the inner one of the electrode layers of the first cell directly faces the inner one of the electrode layers of the second cell across the gas chamber, and gas diffusion restricting means for appropriately restricting diffusion of the gas atmosphere subject to measurement into the gas chamber, the improvement comprising at least one support pillar which is disposed in the gas chamber and is in close contact at its one end with the inner electrode layer of the first solid electrolyte cell and at the opposite end with the inner electrode layer of the second solid electrolyte cell.

2. A gas sensor according to claim 1, wherein the total contact area between said at least one support pillar and each of the electrode layers facing each other across the gas chamber is in the range from 0.8 to 20% of the area of that electrode layer.

3. A gas sensor according to claim 1, wherein said at least one support pillar is formed of a ceramic material.

4. A gas sensor according to claim 3, wherein said ceramic material is selected from the group consisting of alumina, zirconia, mullite and spinel.

5. A gas sensor according to claim 1, wherein the distance between the inner electrode layer of the first cell and the inner electrode layer of the second cell is in the range from 0.01 to 0.2 mm.

6. A gas sensor according to claim 5, wherein said distance is not greater than 0.1 mm.

7. A gas sensor according to claim 5, wherein said at least one support pillar is formed by a thick-film technique on either of the inner electrode layers of the first and second cells.

8. A gas sensor according to claim 1, wherein said spacing means comprises a ceramics board which is cut away through its entire thickness in a selected area so as to provide said gas chamber, said gas diffusion restricting means comprising at least one narrow gas passage formed through a frame-like part of said board.

9. A gas sensor according to claim 8, wherein said gas diffusion restricting means comprises at least one porous member which is fitted into an aperture formed in said frame-like part of the spacing board.

10. A gas sensor according to claim 1, wherein the outer one of the electrode layers of the first solid electrolyte cell comes into contact with a reference gas.

11. A gas sensor according to claim 1, wherein the solid electrolyte plates of the first and second cells are formed of an oxygen ion conductive solid electrolyte.

* * * * *